United States Patent
Carlsson et al.

(10) Patent No.: US 9,858,943 B1
(45) Date of Patent: Jan. 2, 2018

(54) ACCESSIBILITY FOR THE HEARING IMPAIRED USING MEASUREMENT AND OBJECT BASED AUDIO

(71) Applicant: Sony Corporation, Tokyo (JP)

(72) Inventors: Gregory Carlsson, Santee, CA (US); Steven Richman, San Diego, CA (US); James R. Milne, Ramona, CA (US)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/590,795

(22) Filed: May 9, 2017

(51) Int. Cl.
| | |
|---|---|
| *G10L 21/0264* | (2013.01) |
| *H04R 25/00* | (2006.01) |
| *H04R 5/04* | (2006.01) |
| *G10L 21/0364* | (2013.01) |
| *H04S 3/00* | (2006.01) |
| *A61B 5/12* | (2006.01) |
| *H04M 1/725* | (2006.01) |
| *H04S 1/00* | (2006.01) |

(52) U.S. Cl.
CPC .......... *G10L 21/0264* (2013.01); *A61B 5/125* (2013.01); *G10L 21/0364* (2013.01); *H04M 1/72591* (2013.01); *H04R 5/04* (2013.01); *H04R 25/353* (2013.01); *H04S 1/002* (2013.01); *H04S 3/008* (2013.01)

(58) Field of Classification Search
CPC ...... H04R 25/505; H04R 25/552; H04R 5/04; H04R 25/50; H04R 2225/55; H04R 2225/43; A61B 5/121; A61B 5/7415; A61B 5/7475; A61B 5/7257; G10L 21/0364; G10L 21/0208; G10L 21/0232; G10L 21/057
See application file for complete search history.

(56) References Cited

U.S. PATENT DOCUMENTS

| | | |
|---|---|---|
| 6,195,640 B1 | 2/2001 | Mullaly et al. |
| 7,110,951 B1 | 9/2006 | Pedersen et al. |
| 8,494,298 B2 | 7/2013 | Lewis et al. |
| 8,965,216 B2 | 2/2015 | Oshima et al. |

(Continued)

FOREIGN PATENT DOCUMENTS

| | | |
|---|---|---|
| EP | 0701366 A2 | 3/1996 |
| JP | 3037041 B2 | 4/2000 |

(Continued)

OTHER PUBLICATIONS

Kickstarter, "Nura: Headphones that learn and adapt to your unique hearing", launch date May 16, 2016, https://www.kickstarter.com/projects/nura/nura-headphones-that-learn-and-adapt-to-your-unique-hearing.

(Continued)

*Primary Examiner* — Mohammad Islam
(74) *Attorney, Agent, or Firm* — John L. Rogitz

(57) ABSTRACT

A setup application in a TV, sound bar, surround sound speaker system, or AVR creates a hearing profile for a user, calibrating various frequencies according to an interactive calibration step. Then, object-based audio, which may include metadata describing the key aspects of the audio, is used to identify the key aspects so that they can be emphasized, using the calibration information, to allow for increased intelligibility and the most natural listening experience possible for the hearing-impaired. EQ calibration for each speaker also may be effected for each user.

20 Claims, 4 Drawing Sheets

(56) References Cited

U.S. PATENT DOCUMENTS

| | | | |
|---|---|---|---|
| 8,965,546 | B2 | 2/2015 | Visser et al. |
| 9,055,265 | B2 | 6/2015 | Shintani et al. |
| 9,137,484 | B2 | 9/2015 | Difrancesco et al. |
| 9,180,053 | B2 | 11/2015 | Dalal et al. |
| 9,191,767 | B2 | 11/2015 | Hopkins |
| 9,257,114 | B2 | 2/2016 | Tanaka |
| 9,263,027 | B2 | 2/2016 | Hopkins et al. |
| 9,596,555 | B2 | 3/2017 | Kaburlasos et al. |
| 2003/0030752 | A1 | 2/2003 | Begeja et al. |
| 2004/0246272 | A1 | 12/2004 | Ramian |
| 2005/0047624 | A1 | 3/2005 | Kleen |
| 2006/0109242 | A1 | 5/2006 | Simpkins |
| 2006/0125796 | A1 | 6/2006 | Utz et al. |
| 2006/0140420 | A1 | 6/2006 | Machida |
| 2010/0131983 | A1 | 5/2010 | Shannon et al. |
| 2011/0035031 | A1 | 2/2011 | Faenger et al. |
| 2012/0167154 | A1 | 6/2012 | Kim et al. |
| 2012/0324493 | A1 | 12/2012 | Holmdahl et al. |
| 2013/0121515 | A1 | 5/2013 | Hooley et al. |
| 2013/0133022 | A1 | 5/2013 | Bi et al. |
| 2014/0196129 | A1 | 7/2014 | Amin |
| 2014/0254828 | A1 | 9/2014 | Ray et al. |
| 2014/0287779 | A1 | 9/2014 | O'Keefe et al. |
| 2014/0314261 | A1* | 10/2014 | Selig ............ H04R 25/50 381/314 |
| 2015/0045003 | A1 | 2/2015 | Vora et al. |
| 2015/0373295 | A1 | 12/2015 | Outters |
| 2016/0021481 | A1 | 1/2016 | Johnson et al. |
| 2016/0063894 | A1 | 3/2016 | Lee |
| 2016/0078594 | A1 | 3/2016 | Scherlen |
| 2016/0170617 | A1 | 6/2016 | Shi et al. |
| 2016/0239253 | A1* | 8/2016 | Staffaroni ........... G10L 21/0364 |
| 2016/0282624 | A1 | 9/2016 | Munger et al. |

FOREIGN PATENT DOCUMENTS

| | | |
|---|---|---|
| JP | 2008236299 A | 10/2008 |
| KR | 100260702 B1 | 7/2000 |

OTHER PUBLICATIONS

Robert Silva, "The ZVOX AV200 AccuVoice TV Speaker Makes Voices and Dialog Clear", Dec. 20, 2016 https://www.lifewire.com/the-zvox-av200-accuvoice-tv-speaker-makes-voices-and-dialog-clear-4086538?utm_source=emailshare&utm_medium=social&utm_campaign=shareurlbuttons.

Anabel Martin Gonzalez, "Advanced Imaging in Head-Mounted Displays for Patients with Age-Related Macular Degeneration", Dissertation, Technical University of Munich, Jun. 29, 2011 (pp. 1-149).

Carlos Aguilar, Eric Castet, "Evaluation of a gaze-controlled vision enhancement system for reading in visually impaired people", Nice Sophia Antipolis University, Aix Marseille University, Apr. 5, 2017, Nice, France, Marseille, France.

James Ohene-Djan, Rachel Shipsey, "E-Subtitles: Emotional Subtitles as a Technology to assist the Deaf and Hearing-Impaired when Learning from Television and Film.". Goldsmiths College, University of London, 2006, New Cross, London.

John L. Sibert, Mehmet Gokturk, Robert A. Lavine, "The Reading Assistant: Eye Gaze Triggered Auditory Prompting for Reading Remediation", George Washington University, 2000.

Rita Oliveira, Jorge Ferraz De Abreu, Ana Margarida Almeida, "Audio Description in Interactive Television (iTV): proposal of a collaborative and voluntary approach", Department of Communication and Arts, University of Aveiro, Sep. 2016, Aveiro, Portugal.

Robert B. Goldstein, Henry Apfelbaum, Gang Luo and Eli Peli "Dynamic Magnification of Video for People with Visual Impairment", May 2003, The Schepens Eye Research Institute, Harvard Medical School, Boston, MA, USA.

Brant Candelore, Mahyar Nejat, Peter Shintani, "Modifying Display Region for People with Vision Impairment", file history of related U.S. Appl. No. 15/631,669, filed Jun. 23, 2017.

Brant Candelore, Mahyar Nejat, Peter Shintani, "Modifying Display Region for People with Loss of Peripheral Vision", file history of related U.S. Appl. No. 15/645,617, filed Jul. 10, 2017.

Brant Candelore, Mahyar Nejat, Peter Shintani, "Modifying Display Region for People with Macular Degeneration", file history of related U.S. Appl. No. 15/645,796, filed Jul. 10, 2017.

Peter Shintani, Brant Candelore, Mahyar Nejat, "Moving Audio from Center Speaker to Peripheral Speaker of Display Device for Macular Degeneration Accessibility", file history of related U.S. Appl. No. 15/646,550, filed Jul. 11, 2017.

Peter Shintani, Brant Candelore, Mahyar Nejat, "Sensing Viewer Direction of Viewing to Invoke Accessibility Menu in Audio Video Device", file history of related U.S. Appl. No. 15/646,661, filed Jul. 11, 2017.

Peter Shintani, Brant Candelore, Mahyar Nejat, "Quick Accessibility Profiles", file history of related U.S. Appl. No. 15/646,986, filed Jul. 11, 2017.

\* cited by examiner

ACCESSIBILITY FOR THE HEARING IMPAIRED USING MEASUREMENT AND OBJECT BASED AUDIO

FIELD

The present application relates to technically inventive, non-routine solutions that are necessarily rooted in computer technology and that produce concrete technical improvements.

BACKGROUND

Hearing impaired people can experience difficulty hearing audio from display systems such as TVs. Accessibility solutions for the hearing impaired include TV subtitles and hearing aids, both of which are less than optimum. Subtitles not only obscure the video, but require active reading, which distracts from the "lean-back" experience people typically expect from watching TV. Hearing aids can malfunction and in some cases hearing-impaired people might resist using hearing aids.

SUMMARY

Present principles recognize the above problems experienced by hearing-impaired people. Accordingly, in one aspect a device includes at least one computer memory that is not a transitory signal and that in turn includes instructions executable by at least one processor to receive from a user interface (UI) input pertaining to at least first and second speaker frequencies. The instructions are executable to, based at least in part on the input, establish a calibration for the first and second frequencies. The instructions are further executable to identify at least a first audio element in audio comprising at least first and second audio elements, and to modify the first audio element according to the calibration of the first and second frequencies to render a calibrated audio element, but not modify the second audio element according to the calibration of the first and second frequencies. The instructions are executable to play the calibrated audio element and the second audio element on at least one audio speaker.

In some examples the instructions may be executable to modify the first audio element according to the calibration of the first and second frequencies at least in part based on metadata in the audio indicating that the first audio element is an instance of a first type of audio object, whereas the second audio element is not modified according to the calibration of the first and second frequencies at least in part based on metadata in the audio indicating that the second audio element is an instance of a second type of audio object.

In non-limiting implementations the instructions can be executable to modify the first audio element according to the calibration of the first and second frequencies at least in part based on object based audio information indicating that the first audio element is an instance of a first type of audio object. The instructions may be executed to not modify the second audio element according to the calibration of the first and second frequencies at least in part based on object based audio information indicating that the second audio element is an instance of a second type of audio object.

As an example, the first audio element can include speech, qualifying it as a key sound to be modified, whereas the second audio element does not include speech.

In some embodiments the instructions may be executable to establish the calibration at least in part by allowing a user to adjust respective amplitudes of first and second tones played on the speaker at the respective first and second frequencies to achieve what the user perceives as equality in at least one respect between the first and second tones. In such embodiments, the instructions may be executable to modify the first audio element to render the calibrated audio element at least in part by adjusting first and second components having the respective first and second frequencies in the first audio element according to user adjustments of the respective first and second tones.

In examples, the instructions are executable to modify the first audio element according to the calibration of the first and second frequencies at least in part based on metadata in the audio indicating that the first audio element is a key sound as determined by the content provider. The instructions may be executable to not modify the second audio element according to the calibration of the first and second frequencies at least in part based on metadata in the audio indicating that the second audio element is not a key sound.

In some embodiments, first circuitry is configured to modify the first audio element according to the calibration of the first and second frequencies to render the calibrated audio element (CAE). Second circuitry is configured to receive the CAE and modify at least one EQ parameter in the CAE for at least first and second audio channels according to at least one user profile.

In another aspect, a method includes receiving a person's frequency response profile indicating respective first and second perceptions of the person to at least respective first and second frequencies. The method also includes receiving audio comprising first audio objects and second audio objects, and modifying an amplitude of at least one frequency in the first audio objects according to the person's frequency response profile to render modified first audio objects. The method may include not modifying an amplitude at least one frequency in the second audio objects according to the person's frequency response profile. The method then includes playing the modified first audio objects and the second audio objects on at least one audio speaker.

At least one frequency in the first audio objects may be modified based at least in part on identification information in metadata accompanying the audio. The metadata may indicate that the first audio objects are key sounds as determined by the content provider, or it may indicate that the first audio objects are of a type of object matching a key sound type as determined by the audio player.

In another aspect, an audio video assembly (AVA) includes at least one display for presenting video under control of at least one processor, and at least one speaker for presenting audio under control of at least one processor, which may be the same processor controlling the display or a different processor. The assembly also includes at least one storage comprising instructions executable by at least one processor (such as the display processor or speaker processor if different from the display processor) to receive audio having at least first and second components with respective first and second frequencies. The instructions can be executed to change at least a first component in a first object in the audio according to first frequency information in a person's frequency response profile, and also to change at least a second component in the first object in the audio according to second frequency information in the person's frequency response profile. The instructions are executable to play at least the first audio object on the at least one speaker after changing the first and second components.

The details of the present disclosure, both as to its structure and operation, can be best understood in reference to the accompanying drawings, in which like reference numerals refer to like parts, and in which:

DETAILED DESCRIPTION

Figure 1:
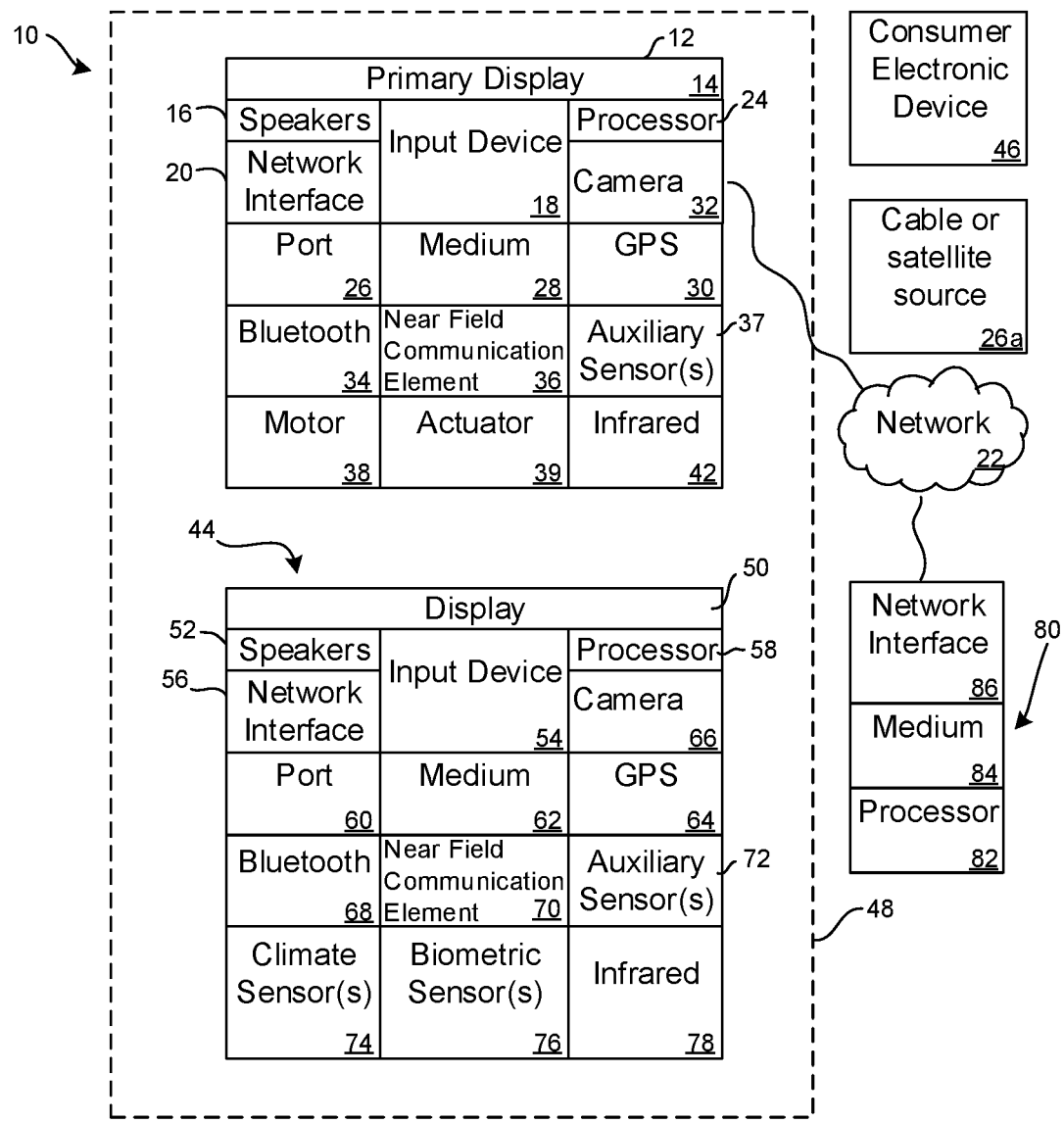
FIG. 1 is a block diagram of an example system including an example in accordance with present principles.

This disclosure relates generally to computer ecosystems including aspects of consumer electronics (CE) device based user information in computer ecosystems. A system herein may include server and client components, connected over a network such that data may be exchanged between the client and server components. The client components may include one or more computing devices including portable televisions (e.g. smart TVs, Internet-enabled TVs), portable computers such as laptops and tablet computers, and other mobile devices including smart phones and additional examples discussed below. These client devices may operate with a variety of operating environments. For example, some of the client computers may employ, as examples, operating systems from Microsoft, or a Unix operating system, or operating systems produced by Apple Computer or Google. These operating environments may be used to execute one or more browsing programs, such as a browser made by Microsoft or Google or Mozilla or other browser program that can access web applications hosted by the Internet servers discussed below.

Servers may include one or more processors executing instructions that configure the servers to receive and transmit data over a network such as the Internet. Or, a client and server can be connected over a local intranet or a virtual private network. A server or controller may be instantiated by a game console such as a Sony Playstation®, a personal computer, etc.

Information may be exchanged over a network between the clients and servers. To this end and for security, servers and/or clients can include firewalls, load balancers, temporary storages, and proxies, and other network infrastructure for reliability and security. One or more servers may form an apparatus that implement methods of providing a secure community such as an online social website to network members.

As used herein, instructions refer to computer-implemented steps for processing information in the system. Instructions can be implemented in software, firmware or hardware and include any type of programmed step undertaken by components of the system.

A processor may be any conventional general purpose single—or multi-chip processor that can execute logic by means of various lines such as address lines, data lines, and control lines and registers and shift registers.

Software modules described by way of the flow charts and user interfaces herein can include various sub-routines, procedures, etc. Without limiting the disclosure, logic stated to be executed by a particular module can be redistributed to other software modules and/or combined together in a single module and/ or made available in a shareable library.

Present principles described herein can be implemented as hardware, software, firmware, or combinations thereof; hence, illustrative components, blocks, modules, circuits, and steps are set forth in terms of their functionality.

Further to what has been alluded to above, logical blocks, modules, and circuits described below can be implemented or performed with a general purpose processor, a digital signal processor (DSP), a field programmable gate array (FPGA) or other programmable logic device such as an application specific integrated circuit (ASIC), discrete gate or transistor logic, discrete hardware components, or any combination thereof designed to perform the functions described herein. A processor can be implemented by a controller or state machine or a combination of computing devices.

The functions and methods described below, when implemented in software, can be written in an appropriate language such as but not limited to C# or C++, and can be stored on or transmitted through a computer-readable storage medium such as a random access memory (RAM), read-only memory (ROM), electrically erasable programmable read-only memory (EEPROM), compact disk read-only memory (CD-ROM) or other optical disk storage such as digital versatile disc (DVD), magnetic disk storage or other magnetic storage devices including removable thumb drives, etc. A connection may establish a computer-readable medium. Such connections can include, as examples, hard-wired cables including fiber optics and coaxial wires and digital subscriber line (DSL) and twisted pair wires.

Components included in one embodiment can be used in other embodiments in any appropriate combination. For example, any of the various components described herein and/or depicted in the Figures may be combined, interchanged or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

Now specifically referring to FIG. 1, an example ecosystem 10 is shown, which may include one or more of the example devices mentioned above and described further below in accordance with present principles. The first of the example devices included in the system 10 is an example primary display device, and in the embodiment shown is an audio video display device (AVDD) 12 such as but not limited to an Internet-enabled TV. Thus, the AVDD 12 alternatively may be an appliance or household item, e.g. computerized Internet enabled refrigerator, washer, or dryer. The AVDD 12 alternatively may also be a computerized Internet enabled ("smart") telephone, a tablet computer, a notebook computer, a wearable computerized device such as e.g. computerized Internet-enabled watch, a computerized Internet-enabled bracelet, other computerized Internet-enabled devices, a computerized Internet-enabled music player, computerized Internet-enabled head phones, a computerized Internet-enabled implantable device such as an implantable skin device, etc. Regardless, it is to be understood that the AVDD 12 is configured to undertake present principles (e.g. communicate with other CE devices to undertake present principles, execute the logic described herein, and perform any other functions and/or operations described herein).

Accordingly, to undertake such principles the AVDD 12 can be established by some or all of the components shown in FIG. 1. For example, the AVDD 12 can include one or more displays 14 that may be implemented by a high definition or ultra-high definition "4K" or "8K" (or higher resolution) flat screen and that may be touch-enabled for receiving consumer input signals via touches on the display. The AVDD 12 may include one or more speakers 16 for outputting audio in accordance with present principles, and at least one additional input device 18 such as e.g. an audio receiver/microphone for e.g. entering audible commands to the AVDD 12 to control the AVDD 12. The example AVDD 12 may also include one or more network interfaces 20 for communication over at least one network 22 such as the Internet, an WAN, an LAN, etc. under control of one or more processors 24. Thus, the interface 20 may be, without limitation, a Wi-Fi transceiver, which is an example of a wireless computer network interface. It is to be understood that the processor 24 controls the AVDD 12 to undertake present principles, including the other elements of the AVDD 12 described herein such as e.g. controlling the display 14 to present images thereon and receiving input therefrom. Furthermore, note the network interface 20 may be, e.g., a wired or wireless modem or router, or other appropriate interface such as, e.g., a wireless telephony transceiver, or Wi-Fi transceiver as mentioned above, etc.

In addition to the foregoing, the AVDD 12 may also include one or more input ports 26 such as, e.g., a USB port to physically connect (e.g. using a wired connection) to another CE device and/or a headphone port to connect headphones to the AVDD 12 for presentation of audio from the AVDD 12 to a consumer through the headphones. The AVDD 12 may further include one or more computer memories 28 that are not transitory signals, such as disk-based or solid state storage (including but not limited to flash memory). Also in some embodiments, the AVDD 12 can include a position or location receiver such as but not limited to a cellphone receiver, GPS receiver and/or altimeter 30 that is configured to e.g. receive geographic position information from at least one satellite or cellphone tower and provide the information to the processor 24 and/or determine an altitude at which the AVDD 12 is disposed in conjunction with the processor 24. However, it is to be understood that that another suitable position receiver other than a cellphone receiver, GPS receiver and/or altimeter may be used in accordance with present principles to e.g. determine the location of the AVDD 12 in e.g. all three dimensions.

Continuing the description of the AVDD 12, in some embodiments the AVDD 12 may include one or more cameras 32 that may be, e.g., a thermal imaging camera, a digital camera such as a webcam, and/or a camera integrated into the AVDD 12 and controllable by the processor 24 to gather pictures/images and/or video in accordance with present principles. Also included on the AVDD 12 may be a Bluetooth transceiver 34 and other Near Field Communication (NFC) element 36 for communication with other devices using Bluetooth and/or NFC technology, respectively. An example NFC element can be a radio frequency identification (RFID) element.

Further still, the AVDD 12 may include one or more auxiliary sensors 37 (e.g., a motion sensor such as an accelerometer, gyroscope, cyclometer, or a magnetic sensor, an infrared (IR) sensor, an optical sensor, a speed and/or cadence sensor, a gesture sensor (e.g. for sensing gesture command, etc.) providing input to the processor 24. The AVDD 12 may include still other sensors such as e.g. one or more climate sensors 38 (e.g. barometers, humidity sensors, wind sensors, light sensors, temperature sensors, etc.) and/or one or more biometric sensors 40 providing input to the processor 24. In addition to the foregoing, it is noted that the AVDD 12 may also include an infrared (IR) transmitter and/or IR receiver and/or IR transceiver 42 such as an IR data association (IRDA) device. A battery (not shown) may be provided for powering the AVDD 12.

Still referring to FIG. 1, in addition to the AVDD 12, the system 10 may include one or more other CE device types. In one example, a first CE device 44 may be used to control the display via commands sent through the below-described server while a second CE device 46 may include similar components as the first CE device 44 and hence will not be discussed in detail. In the example shown, only two CE devices 44, 46 are shown, it being understood that fewer or greater devices may be used.

In the example shown, to illustrate present principles all three devices 12, 44, 46 are assumed to be members of an entertainment network in, e.g., in a home, or at least to be present in proximity to each other in a location such as a house. However, for illustrating present principles the first CE device 44 is assumed to be in the same room as the AVDD 12, bounded by walls illustrated by dashed lines 48.

The example non-limiting first CE device 44 may be established by any one of the above-mentioned devices, for example, a portable wireless laptop computer or notebook computer, and accordingly may have one or more of the components described below. The second CE device 46 without limitation may be established by a wireless telephone. The second CE device 46 may implement a portable hand-held remote control (RC).

The first CE device 44 may include one or more displays 50 that may be touch-enabled for receiving consumer input signals via touches on the display. The first CE device 44 may include one or more speakers 52 for outputting audio in accordance with present principles, and at least one additional input device 54 such as e.g. an audio receiver/microphone for e.g. entering audible commands to the first CE device 44 to control the device 44. The example first CE device 44 may also include one or more network interfaces 56 for communication over the network 22 under control of one or more CE device processors 58. Thus, the interface 56 may be, without limitation, a Wi-Fi transceiver, which is an example of a wireless computer network interface. It is to be understood that the processor 58 may control the first CE device 44 to undertake present principles, including the other elements of the first CE device 44 described herein such as e.g. controlling the display 50 to present images thereon and receiving input therefrom. Furthermore, note the network interface 56 may be, e.g., a wired or wireless modem or router, or other appropriate interface such as, e.g., a wireless telephony transceiver, or Wi-Fi transceiver as mentioned above, etc.

In addition to the foregoing, the first CE device 44 may also include one or more input ports 60 such as, e.g., a USB port to physically connect (e.g. using a wired connection) to another CE device and/or a headphone port to connect headphones to the first CE device 44 for presentation of audio from the first CE device 44 to a consumer through the headphones. The first CE device 44 may further include one or more computer memories 62 such as disk-based or solid state storage. Also in some embodiments, the first CE device 44 can include a position or location receiver such as but not limited to a cellphone and/or GPS receiver and/or altimeter 64 that is configured to e.g. receive geographic position information from at least one satellite and/or cell tower, using triangulation, and provide the information to the CE device processor 58 and/or determine an altitude at which the first CE device 44 is disposed in conjunction with the CE device processor 58. However, it is to be understood that that another suitable position receiver other than a cellphone and/or GPS receiver and/or altimeter may be used in accordance with present principles to e.g. determine the location of the first CE device 44 in e.g. all three dimensions.

Continuing the description of the first CE device 44, in some embodiments the first CE device 44 may include one or more cameras 66 that may be, e.g., a thermal imaging camera, a digital camera such as a webcam, and/or a camera integrated into the first CE device 44 and controllable by the CE device processor 58 to gather pictures/images and/or video in accordance with present principles. Also included on the first CE device 44 may be a Bluetooth transceiver 68 and other Near Field Communication (NFC) element 70 for communication with other devices using Bluetooth and/or NFC technology, respectively. An example NFC element can be a radio frequency identification (RFID) element.

Further still, the first CE device 44 may include one or more auxiliary sensors 72 (e.g., a motion sensor such as an accelerometer, gyroscope, cyclometer, or a magnetic sensor, an infrared (IR) sensor, an optical sensor, a speed and/or cadence sensor, a gesture sensor (e.g. for sensing gesture command, etc.) providing input to the CE device processor 58. The first CE device 44 may include still other sensors such as e.g. one or more climate sensors 74 (e.g. barometers, humidity sensors, wind sensors, light sensors, temperature sensors, etc.) and/or one or more biometric sensors 76 providing input to the CE device processor 58. In addition to the foregoing, it is noted that in some embodiments the first CE device 44 may also include an infrared (IR) transmitter and/or IR receiver and/or IR transceiver 78 such as an IR data association (IRDA) device. A battery (not shown) may be provided for powering the first CE device 44.

The second CE device 46 may include some or all of the components shown for the CE device 44.

Now in reference to the afore-mentioned at least one server 80, it includes at least one server processor 82, at least one computer memory 84 such as disk-based or solid state storage, and at least one network interface 86 that, under control of the server processor 82, allows for communication with the other devices of FIG. 1 over the network 22, and indeed may facilitate communication between servers and client devices in accordance with present principles. Note that the network interface 86 may be, e.g., a wired or wireless modem or router, Wi-Fi transceiver, or other appropriate interface such as, e.g., a wireless telephony transceiver.

Accordingly, in some embodiments the server 80 may be an Internet server, and may include and perform "cloud" functions such that the devices of the system 10 may access a "cloud" environment via the server 80 in example embodiments. Or, the server 80 may be implemented by a game console or other computer in the same room as the other devices shown in FIG. 1 or nearby.

Figure 2:
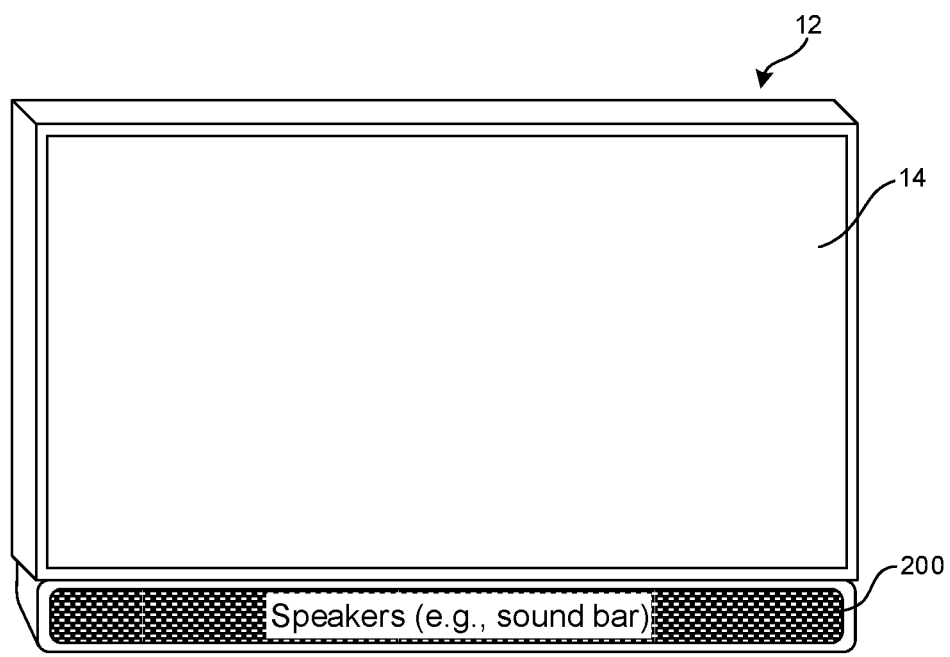
FIG. 2 is a schematic diagram of the audio video display device (AVDD) shown in FIG. 1, illustrating speakers.

FIG. 2 shows that the AVDD 12 may include one or more speakers 200, in some example non-limiting embodiments configured as a Sony sound bar. Other speaker systems are envisioned, such as built-in TV speakers, audio video receivers (AVR), a surround sound system (e.g., a sound bar plus additional surround-sound speakers or an AVR with multiple speakers), etc.

Figure 3:
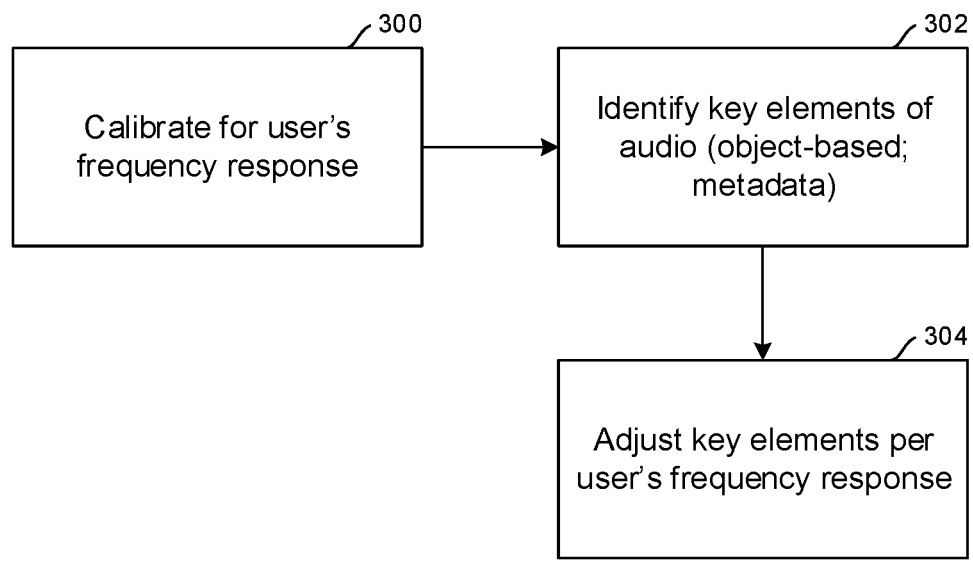
FIG. 3 is a flow chart of example logic according to present principles.

FIG. 3 illustrates example logic for customizing the output of the speaker(s) 200 for individual users. Commencing at block 300, a particular user's frequency response is calibrated using, e.g., the example calibration user interface (UI) discussed below in relation to FIG. 4. In other words, block 300 seeks to determine which frequencies a particular person hears well and which frequencies he or she may suffer a deficit in perceiving. Block 300 assumes for simplicity of disclosure that only a single person is the subject of the frequency tailoring discussed below, it being understood that the logic may be executed for multiple users, whose frequency responses can be maintained in user profiles stored by the AVDD 12 or cloud server 80 or other device and then used to automatically configure the settings of the AVDD 12 or other device employed by the user(s) to play audio. A group profile may be generated if desired to accommodate multiple users by averaging their frequency responses, for example, so that a group profile may be invoked to establish audio settings of the player device according to the group profile when multiple people are present.

After calibration for the user's own personal frequency response, the logic moves to block 302 to identify key or primary aspects of the audio content-typically voices—using object-based audio information. This may be done dynamically as an audio stream is received and buffered just prior to playing the stream. Object-based audio recognition can include using metadata in audio such as is provided by Dolby Atmos® or DTS:X™ to identify the key sounds. Note that metadata may be tailored to the hearing-impaired by identifying, in the metadata, which sounds are "key sounds" as determined by the content provider.

Once the key sound(s) in audio are identified at block 302, the logic moves to block 304 to adjust the frequencies of the key sounds, but not other sounds in the audio, to match the user's frequency response profile. However, in some implementations, if desired both key sounds and non-key sounds may be adjusted according to the user's frequency response profile.

For example, if the user's frequency response profile indicates that the user has more difficulty perceiving lower frequencies than higher frequencies, lower frequencies in the key sounds are increased in amplitude, while higher frequencies are not. The specific frequencies being adjusted match as closely as possible corresponding frequencies in the user's response profile and then played on speakers. In this way, key sounds in audio are dynamically adjusted to make those key sounds as clear as possible for the user based on his individual hearing profile as calibrated at block 300.

Figure 4:
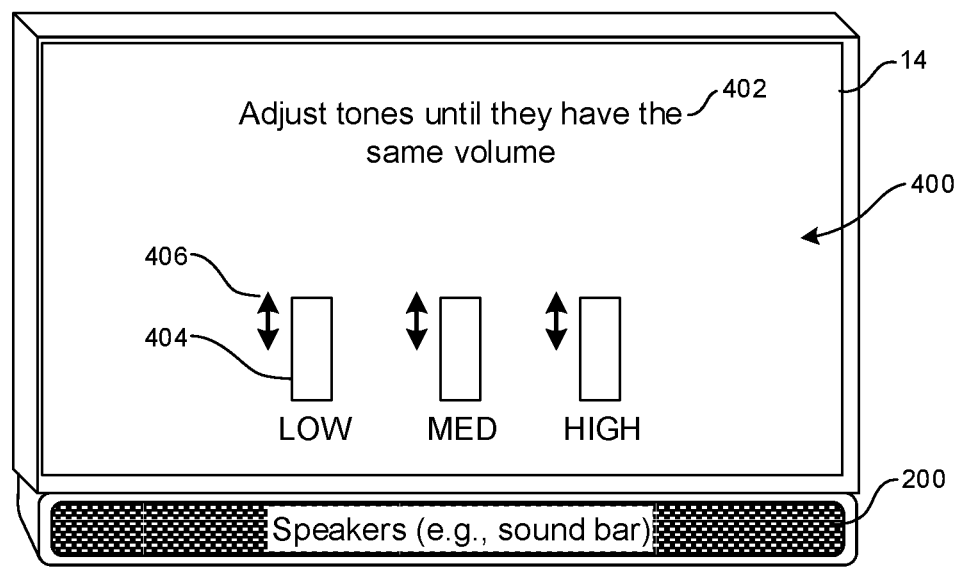
FIG. 4 is a screen shot of an example user interface (UI) related to the logic of FIG. 3.

FIG. 4 illustrates a setup UI 400 that may be presented on, e.g., the display 14 of the AVDD 12. It is to be understood that additionally or equivalently, the UI 400 may be presented on the speaker(s) 16/200 of the AVDD 12 (or other speakers). The UI 400 may additionally or alternatively be presented on an audio video recorder (AVR) associated with the AVDD or other device in a home network, such as a smart phone or tablet computer.

The UI 400 may include a prompt 402 for the user to adjust tones, depicted in the non-limiting example shown as bars 404 that can be lengthened or shortened as shown by the arrows 406, until the user perceives all tones to have the same volume. For example, the low tone in FIG. 4 can be played on speakers, and the user, by means of using a touch screen 14 or arrow keys on a remote control communicating with the AVDD or other appropriate input device, can drag and drop the top edge of the bar 404 corresponding to the low frequency up or down to increase or decrease, respectively, the height of the bar 40 and the corresponding volume of the low tone.

The user can then be prompted to move a screen cursor to another bar 404 of another frequency and repeat the process, until all frequencies (only three shown in FIG. 4 for clarity) have been adjusted by the user to thereby establish the user's individual frequency response profile, for use as described above in relation to FIG. 3 to dynamically adjust individual frequencies in key sounds in audio prior to playing the adjusted audio. The user can be allowed to go back and forth between adjustments, re-adjusting some frequencies after having adjusted others, to fine tune the frequency response profile. In this way, the closest match between amplitudes of multiple frequencies, as perceived by the user, can be achieved.

Figure 5:
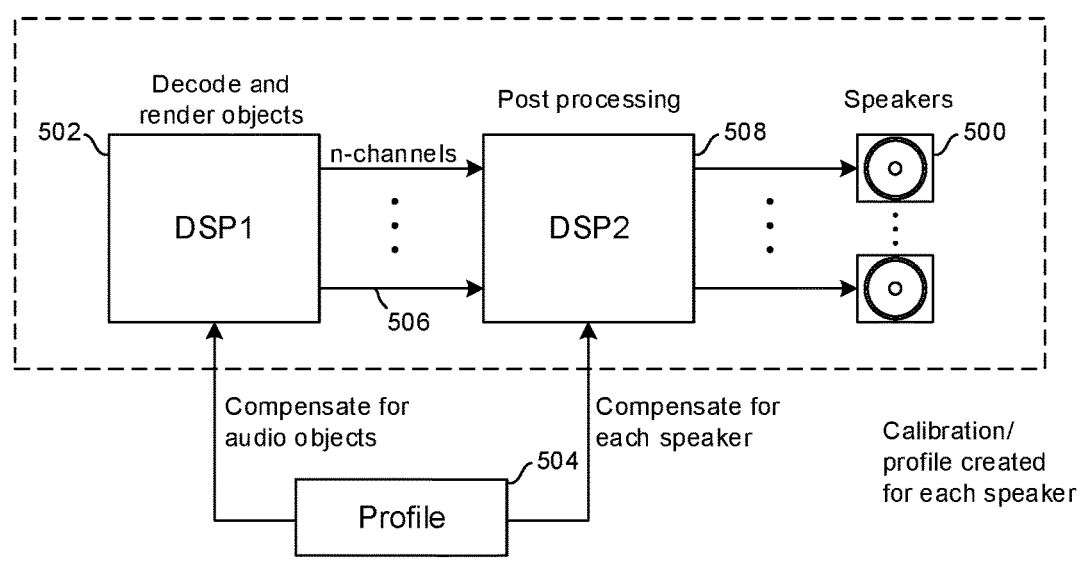
FIG. 5 is a block diagram of an example system that applies a two-step calibration process.

FIG. 5 illustrates a system having plural speakers 500 such as a surround-sound system in which the above-described calibration process is executed not just for audio objects as described, but also for speaker compensation. In other words, the user's frequency response profile can also include EQ (i.e., amplitude, frequency, et al.) compensation for each speaker tailored for the particular user. In such an embodiment, the above-described audio object calibration is executed for each speaker 500, given the location of the speaker, with EQ variables being adjusted for each speaker to best suit the particular user. Note that the second (EQ) portion of the calibration process may be dynamic, such that if speakers are added or removed, the system can be aware of this and adapt for the addition or subtraction of acoustical power and frequency. Principles set forth in the present assignee's U.S. Pat. Nos. 9,560,449, 9,426,551, 9,402,145, 9,369,801, and 9,288,597, incorporated herein by reference, may be used for this purpose.

As shown in FIG. 5, first circuitry 502, which may be implemented in some examples by a digital signal processor (DSP), receives audio objects and decodes and renders the objects. The above-described object calibration parameters from the user's profile 504 are input to the first circuitry 502 and used by the first circuitry 502 to output the objects in accordance with disclosure above. Note that the user's profile 504 may be stored locally to the first circuitry 502 and/or stored in the cloud for provisioning to the first circuitry 502 via a network. A factory default profile may be provided to be used in the absence of a user-configured profile.

The first circuitry 502 outputs the audio in "N" channels 506, wherein "N" is an integer greater than one, to second circuitry 508, which also may be implemented by a DSP. The second circuitry 508 receives the EQ calibration information for the particular user for each of the "N" speakers 500 from the user's profile 504, applying the EQ calibration information to the input received from the first circuitry 502 to each of the "N" channels and outputting the "N" channels, now modified by the EQ calibration information from the user's profile 504, to the "N" speakers 500 for rendering thereof (by playing the audio on the speakers).

While particular techniques are herein shown and described in detail, it is to be understood that the subject matter which is encompassed by the present application is limited only by the claims.

What is claimed is:

1. A device comprising:
   at least one computer memory that is not a transitory signal and that comprises instructions executable by at least one processor to:
   receive from a user interface (UI) input pertaining to at least first and second speaker frequencies;
   based at least in part on the input, establish a calibration for the first and second frequencies;
   identify at least a first audio element in audio comprising at least first and second audio elements;
   modify the first audio element according to the calibration of the first and second frequencies to render a calibrated audio element and not modify the second audio element according to the calibration of the first and second frequencies; and
   play the calibrated audio element and the second audio element on at least one audio speaker.

2. The device of claim 1, comprising the at least one processor.

3. The device of claim 1, comprising the at least one audio speaker.

4. The device of claim 1, wherein the instructions are executable to:
   modify the first audio element according to the calibration of the first and second frequencies at least in part based on metadata in the audio indicating that the first audio element is an instance of a first type of audio object; and
   not modify the second audio element according to the calibration of the first and second frequencies at least in part based on metadata in the audio indicating that the second audio element is an instance of a second type of audio object.

5. The device of claim 1, wherein the instructions are executable to:
   modify the first audio element according to the calibration of the first and second frequencies at least in part based on object based audio information indicating that the first audio element is an instance of a first type of audio object; and
   not modify the second audio element according to the calibration of the first and second frequencies at least in part based on object based audio information indicating that the second audio element is an instance of a second type of audio object.

6. The device of claim 1, wherein the first audio element includes speech and the second audio element does not include speech.

7. The device of claim 1, wherein the instructions are executable to establish the calibration at least in part by:
   allowing a user to adjust respective amplitudes of first and second tones played on the speaker at the respective first and second frequencies to achieve what the user perceives as equality in at least one respect between the first and second tones.

8. The device of claim 7, wherein the instructions are executable to modify the first audio element to render the calibrated audio element at least in part by adjusting first and second components having the respective first and second frequencies in the first audio element according to user adjustments of the respective first and second tones.

9. The device of claim 1, wherein the instructions are executable to:
   modify the first audio element according to the calibration of the first and second frequencies at least in part based on metadata in the audio indicating that the first audio element is a key sound; and
   not modify the second audio element according to the calibration of the first and second frequencies at least in part based on metadata in the audio indicating that the second audio element is not a key sound.

10. The device of claim 1, comprising:
    at least first circuitry configured to modify the first audio element according to the calibration of the first and second frequencies to render the calibrated audio element (CAE); and at least second circuitry configured to receive the CAE and modify at least one EQ parameter in the CAE for at least first and second audio channels according to at least one user profile.

11. A method, comprising:
receiving a person's frequency response profile indicating respective first and second perceptions of the person to at least respective first and second frequencies;
receiving audio comprising first audio objects and second audio objects;
modifying an amplitude of at least one frequency in the first audio objects according to the person's frequency response profile to render modified first audio objects;
not modifying an amplitude at least one frequency in the second audio objects according to the person's frequency response profile; and
playing the modified first audio objects and the second audio objects on at least one audio speaker.

12. The method of claim 11, wherein at least one frequency in the first audio objects is modified based at least in part on identification information in metadata accompanying the audio.

13. The method of claim 12, wherein the metadata indicates that the first audio objects are key sounds.

14. The method of claim 12, wherein the metadata indicates that the first audio objects are of a type of object matching a key sound type.

15. An audio video assembly (AVA), comprising:
at least one display for presenting video under control of at least one processor;
at least one speaker for presenting audio under control of at least one processor; and
at least one storage comprising instructions executable by at least one processor to:
receive audio having at least first and second components with respective first and second frequencies;
change at least a first component in a first object in the audio according to first frequency information in a person's frequency response profile;
change at least a second component in the first object in the audio according to second frequency information in the person's frequency response profile; and
play at least the first audio object on the at least one speaker after changing the first and second components.

16. The AVA of claim 15, wherein the first and second components include volumes.

17. The AVA of claim 15, wherein the instructions are executable to:
not change any component in a second object in the audio according to the person's frequency response profile.

18. The AVA of claim 15, wherein the components in the first object are changed based at least in art on metadata in the audio.

19. The AVA of claim 18, wherein the metadata indicates that the first audio object is a key sound.

20. The AVA of claim 18, wherein the metadata indicates that the first audio object is of a type of object matching a key sound type.

* * * * *